United States Patent [19]

Adachi et al.

[11] Patent Number: 4,584,009

[45] Date of Patent: Apr. 22, 1986

[54] HERBICIDAL COMPOSITIONS CONTAINING SALINOMYCIN

[75] Inventors: Meiro Adachi; Kenji Hamada, both of Kanagawa, Japan

[73] Assignee: Pfizer Inc., New York, N.Y.

[21] Appl. No.: 681,059

[22] Filed: Dec. 13, 1984

[30] Foreign Application Priority Data

Dec. 15, 1983 [JP] Japan .................................. 58-237130

[51] Int. Cl.[4] ............................................ A01N 43/08
[52] U.S. Cl. .................................... 71/88; 71/DIG. 1
[58] Field of Search ............................................ 71/88

[56] References Cited

U.S. PATENT DOCUMENTS 3,857,948  12/1974  Tanaka et al. ...................... 424/283

FOREIGN PATENT DOCUMENTS 51-57820   5/1976  Japan .
1378414  12/1974  United Kingdom .

OTHER PUBLICATIONS

Myiazaki et al., J. Antibiotic, vol. 27, (1974), p. 814.

Primary Examiner—Catherine L. Mills
Attorney, Agent, or Firm—Charles J. Knuth; Peter C. Richardson; James H. Monroe

[57] ABSTRACT

Herbicidal compositions containing salinomycin for the control of weeds are disclosed.

7 Claims, No Drawings

HERBICIDAL COMPOSITIONS CONTAINING SALINOMYCIN

BACKGROUND OF THE INVENTION

This invention relates to a herbicidal composition containing, as active ingredient, a compound selected from the group consisting of salinomycin, esters and salts thereof.

A variety of herbicides have been used in order to protect paddy and upland fields from damage caused by weeds and grasses and to obtain increased crop yields. Recently, focus has been placed on the development of a herbicide capable of selectively killing weeds without doing any harm to crops when applied to useful crops and weeds simultaneously. However, the need still exists for a superior herbicide that is highly active against a wide range of weed species and applicable over prolonged period of treatment.

In efforts to find new and improved herbicidal agents possessing the above-stated properties, it has now been found that a compound selected from the group consisting of salinomycin, esters and salts thereof is very active as a herbicidal agent against paddy weeds, broad-leaf weeds, and perennial weeds when applied to paddy fields or upland fields, and it does not cause any harm to crops.

SUMMARY OF THE INVENTION

The present invention comprises a herbicidal composition having as the active ingredient a compound selected from salinomycin and its herbicidally acceptable esters and salts, together with a herbicidally acceptable carrier. Preferred esters include lower alkyl esters of from 1-6 carbon atoms and preferred salts include alkali metal, alkaline earth metal and ammonium salts, especially the sodium and potassium salts. The compositions wherein the active ingredient is in the form of a mycelial filter cake or is in substantially pure form are both preferred. The composition wherein the active ingredient is present in an amount of from about 2–80 parts by weight of total composition is preferred.

A method of controlling weeds comprising contacting with a herbicidally effective amount of a compound selected from salinomycin and its herbicidally effective esters and salts is also a feature of this invention. The method wherein the compound is admixed with a herbicidally acceptable carrier and is employed at from about 10–1000 g. of compound per 10 ares is preferred. The method wherein the herbicidally effective amount is from about 50–400 g. of compound per 10 ares is especially preferred. The method wherein the weeds are perennial paddy weeds and wherein the compound is employed in dry form or in the form of an aqueous suspension is also preferred.

DETAILED DESCRIPTION OF THE INVENTION

Salinomycin is an antibiotic produced by fermenting strains of *Streptomyces albus* No. 80,614 (ATCC Accession No. 21838, FRI Accession No. 419). Isolation and characterization of the antibiotic is disclosed in U.S. Pat. No. 3,857,948, and Miyazaki et. al., J. Antibiotic 27, 814 (1974). Salinomycin belongs to a class of antibiotics referred to as polyether antibiotics and is active against Gram-positive bacteria, fungi and protozoa. Specifically, salinomycin exhibits excellent anticoccidial activity and is very effective in the control of coccidiosis in poultry and cattle. The acaricidal activity of salinomycin is known as described in Japan Kokai No. 51-57,820. However, no herbicidal activity has been reported for this substance.

In accordance with this invention, it has been unexpectedly found that salinomycin is of particular value in controlling weeds. The herbicidal compositions of this invention are ones containing as active ingredient, salinomycin, esters thereof, salts thereof, or mixtures of these compounds.

Suitable esters include lower alkyl esters having from 1 to 6 carbon atoms. Suitable salts include alki metal salts, for example, sodium or potassium salts, alkaline earth metal salts, such as calcium or magnesium salts and ammonium salts. Salinomycin for use in this invention may be prepared by methods well known in the art, for example, as described in U.S. Pat. No. 3,857,948.

The active compound may be used in this invention either as the pure compound or in a form such as the mycelial filter cake which contains the active compound or the crude product which is prepared from fermentation broth. The use of the later two is advantageous in terms of economy when compared to the application of the pure substance.

Effectively controllable weeds by this invention include paddy weeds; *Monochoria vaginalis, Ammannia multiflora, Cyperus difformis, Rotala indica Koehne, Cyperus serotinus, Scripus juncoides, Sagitaria pygmaea* and other annual weeds; upland weeds; and *Portulaca oleracea* and *Amaranthus lividus*. In particular, the herbicidal compositions of this invention can effectively control perennial paddy weeds including *Cyperus serotinus, Scripus juncoides* and *Sagitaria pygmaea* that have been hitherto uncontrollable by the presently-known herbicides. Furthermore, the herbicidal compositions of this invention are active against weeds in advanced stages of growth and also applicable in a wide range of weed species.

In accord with this invention, the herbicidal compositions may be applied to paddy fields or upland fields, before or after weed emergence. As for methods of application, the soil can be treated before the weed emergence, or the weeds can be treated after emergence. Thus, this invention will enable the appropriate period of weed treatment to be extended beyond the presently-recognized period. The effective amount of the active compound is from about 10 to 1,000 g per 10 ares of upland or paddy field, preferably about 50 g to 400 g per 10 ares. However, the optimum dosage of the active compound will vary according to the method of application, purpose of use, weather conditions, soil conditions, and the conditions of weeds, etc., and will not be limited to the above range.

The active compound may be applied alone or in combination with herbicidally-acceptable carriers or diluents. For practical purposes, the compounds can be combined with suitable carriers or diluents to form powders, granules, microgranules, wettable powders, aqueous suspensions, emulsifiable concentrates and the like. Example of suitable solid carriers include talc, bentonite, clay, kaoline silica, and potassium carbonate. Examples of suitable liquid carriers include alcohol, ethyl acetate, acetone, dimethylsulfoxide, cyclohexanone, and xylene. Examples of suitable emulsifying agents include alkyl sulfates, alkylsulfonic acid salts, polyethyleneglycol ethers, and polyhydroxyalcohol esters. The herbicidal compositions of this invention may contain from about 10 to 80 parts by weight of the active ingredient in the form of wettable powders; from about 10 to 50 parts by weight in the form of emulsions; from about 2 to 10 parts by weight in the form of powders; and from about 2 to 20 parts by weight in the form of granules.

The instant compositions can be applied to upland or paddy fields in combination with insecticides, fungicides and/or other herbicides. When combined with other herbicides or active ingredients thereof, they may exhibit an enhanced or wider range of activity.

The present invention is illustrated by the following examples. However it should be understood that the invention is not limited to the specific details of these examples.

EXAMPLE 1

The following ingredients were combined and ground to provide a wettable powder composition:

| Ingredients | Parts by Weight |
| --- | --- |
| Salinomycin | 30 |
| Diatomaceous earth | 65 |
| Sodium alkylbenzenesulfonate | 3 |
| Polyvinyl alcohol | 2 |

EXAMPLE 2

The following ingredients were combined and blended well by addition of water, and spheronized by a granulator to provide a granule composition:

| Ingredients | Parts by Weight |
| --- | --- |
| Salinomycin | 2 |
| Bentonite | 12 |
| Clay | 85.5 |
| Sodium lignin sulfonate | 0.5 |

EXAMPLE 3

The following ingredients were combined and blended to provide an emulsifiable concentrate composition:

| Ingredients | Parts by Weight |
| --- | --- |
| Salinomycin | 20 |
| Polyethylenegycol ether | 10 |
| Cyclohexanone | 40 |
| Xylene | 30 |

Test 1

Herbicidal Activity against Annula Paddy Weeds

Post-Emergence Soil Treatment

Wagner pots (1/2000 are) were filled with paddy field soil and annual paddy weed seeds were planted therein. Pots were maintained under submerged conditions during a period of two weeks after the seeding. The emulsifiable concentrate composition prepared according to Example 3 was diluted with water and applied to the soil at various levels of the active ingredient as tabulated in Table 1.

Herbicidal activity was observed with the naked eyes five weeks after the soil treatment by comparing the herbicide-treated group with the non-treated control group. The test results are shown in Table 1 where herbicidal activity is expressed in terms of the following standards.

5—completely killed
4—severely damaged
3—moderately damaged
2—mildly damaged
1—slightly damaged
0—non-damaged In this test, SATURN-S granule (active ingredients: benthiocarb 7%; simetryne 1.5%) was used as a reference herbicidal agent.

TABLE 1

| Weeds (Leaf Stage of Growth) | Herbicidal Agent Dosage (g/10 ares) Salinomycin(emulsion) | | | | SATURN-S |
| --- | --- | --- | --- | --- | --- |
| | 100* | 200* | 300* | 1000** | 2000** |
| Echinchloa oryzicola (1.0–1.8) | 1 | 2 | 2 | 5 | 5 |
| Monochoria vaginalis (1.0) | 4 | 4 | 4 | 4 | 5 |
| Ammannia Multiflora (1.0) | 3 | 3 | 4 | 5 | 5 |
| Cyperus Difformis (1.0) | 4 | 4 | 5 | 5 | 5 |
| Rotala Indica (1.0) | 4 | 5 | 5 | 5 | 5 |
| Others | 2 | 5 | 5 | 5 | 5 |

*Amount of active ingredients used.
**Amount of formulated granules used.

The above test results indicate that the herbicidal composition of this invention is as active as SATURN-S except in the case of *Echinochla oryzicola*.

Test 2

Herbicidal Activity against Perennial Paddy Weeds

Post-Emergence Soil Treatment

Wagner pots (1/2000 are) were filled with paddy field soil, and after sprinkling water, seeds of *Scripus juncoides* were planted in the pots. Five tubers of *Sagitaria pygmaea* or *Cyperus serotinus* were planted in a pot. Pots were then maintained under submerged conditions during a period of ten days after the seeding. The emulsifiable concentrate composition prepared according to Example 3 was diluted with water and applied to the soil with various levels of the active ingredient as tabulated in Table 2.

TABLE 2

| Herbicidal Agent | Dosage (a.i.* g/10 ares) | Test Weeds (Leaf stage of growth) | | |
| --- | --- | --- | --- | --- |
| | | Cyperus serotinus | Scripus juncoides | Sagitaria pygmaea |
| | | (0–2.0) | (1.5) | (0–) |
| Salinomycin (emulsion) | 300 | 2 | 2 | 2 |
| | 900 | 4 | 4 | 5 |
| Benthiocarb | 300 | 4 | 3 | 0 |
| | 900 | 4 | 5 | 0 |

*Amount of active ingredients used.

As is clear from the results of Table 2, the herbicidal composition of this invention exhibits satisfactory herbicidal activity against a variety of perennial paddy weeds. Of particular note is its marked controlling effects on *Sagitaria pygmaea* against which benthiocarb is ineffective.

Test 3

Herbicidal Activity against Perennial Paddy Weeds

Post-Emergence Foliar Treatment

Wagner pots (1/2000 arce) were filled paddy field soil and kept in a greenhouse. Seeds of *Scripus juncoides*, tubers of *Sagitaria pygmaea* and tubers of *Cyperus serotinus* were planted in pots, and the pots were kept under submerged conditions with water 2 cm. in depth. On the same day, the emulsifiable concentrate composition prepared according to Example 3 was diluted with water and applied to the soil with various levels of the active ingredient.

Herbicidal activity was assessed four weeks after the soil treatment in a manner similar to that described in Test 1. The test results are shown in Table 3. In this test, benthiocarb was used as a reference herbicidal agent.

TABLE 3

| Herbicidal Agent | Dosage (a.i. g/10 ares) | Cyperus serptinus | Scripus juncoides | Sagitaria pygmaea |
|---|---|---|---|---|
| Salinomycin | 300 | 3 | 5 | 4 |
|  | 900 | 4 | 5 | 5 |
| Benthiocarb | 300 | 4 | 5 | 0 |
|  | 900 | 5 | 5 | 0 |

Test 4

Herbicidal Activity against Upland Weeds

Pre-Emergence Soil Treatment

Seeding pots (6×15×10 cm) were filled with 500 g of upland soil per pot and 0.5 g of synthetic fertilizer (N:P:K=14:14:14) was added thereto. Seeds of *Amaranthus lividus* and *Portulaca oleracea* were planted in a pot; and three grains of wheat and corn were also planted in each pot, and the pots were covered with soil. On the following day, the salinomycin wettable powder prepared according to Example 1 was suspended in water and applied to the soil at a level of 100 g, 200 g, or 400 g per 10 ares based on the amount of the active ingredient in such a manner that a total amount of 200 l of water containing the salinomycin composition was sprayed on 10 ares of land at each level.

Following the procedure of Test 1, herbicidal activity was assessed 14 days after the soil-treatment. Damage to the test crops caused by the composition of this invention was also assessed and judged in terms of the standards as shown below:

—; no damage
±; slight damage
+; minor damage
++; moderate damage
+++; heavy damage
x; killed In this test, alachlor (2-chloro-N-(2,6-diethylphenyl)-N-(methoxymethyl acetamide)) was used as a reference herbicidal agent. The test results are shown in Table 4.

TABLE 4

| Herbicidal Agent | Dosage (a.i. g/10 ares) | Test Weeds | | Crops | |
|---|---|---|---|---|---|
| | | Amaranthus lividus | Portulaca oleracea | Wheat | Corn |
| Salinomycin | 100 | 1 | 2 | — | — |
|  | 200 | 3 | 5 | — | — |
|  | 400 | 4 | 5 | — | — |
| Alachlor | 100 | 3 | 5 | — | — |
|  | 200 | 4 | 5 | — | — |
|  | 400 | 5 | 5 | — | — |

The above results indicate that the herbicidal composition of this invention is effective at a level higher than 200 g a.i. per 10 ares with no damage to the test crops at all.

Test 5

Herbicidal Activity against Upland Weeds

Post-Emergence Foliar Treatment

Following the method in Test 4, seeds of the weeds, wheat, corn and soya beans were planted in pots and grown under the controlled conditions. When the weeds reached the 2nd or 3rd leaf stage, the salinomycin wettable powder prepared according to Example 1 was suspended with water and sprayed on the leaves at a level of 100 g, 200 g, or 400 g per 10 ares, based on the amount of the active ingredient, in such a manner that a total amount of 200 l of water containing the salinomycin composition was sprayed on 10 ares of upland at each level.

Following the procedure of Example 7, herbicidal activity as well as damage to the crops were assessed 14 days after the treatment. In this test, alachlor and 2,4-D(2,4-dichlorophenoxyacetic acid) were used as reference herbicidal agents. The test results are shown in Table 5.

TABLE 5

| Herbicidal Agent | Dosage (g a.i./10 ares) | Amaranthus lividus | Portulaca oleracea | Wheat | Corn | Soya beans |
|---|---|---|---|---|---|---|
| Salinomycin | 100 | 2 | 2 | — | — | ± |
|  | 200 | 4 | 4 | — | — | ± |
|  | 400 | 4 | 5 | — | — | ± |
| Alachlor | 100 | 0 | 0 | — | — | — |
|  | 200 | 0 | 0 | — | — | — |
|  | 400 | 0 | 0 | — | — | — |
| 2.4-D | 100 | 5 | 5 | — | — | x |
|  | 200 | 5 | 5 | — | — | x |
|  | 400 | 5 | 5 | — | — | x |

The above results indicate that the herbicidal composition of this invention is effective against farmland weeds at a level higher than 200 g a.i. per 10 ares and does not damage wheat and corn.

We claim:

1. A method of controlling weeds comprising contacting said weeds with a herbicidally effective amount of a compound selected from salinomycin and its herbicidally effective esters and salts.

2. The method of claim 1 wherein said compound is admixed with a herbicidally acceptable carrier.

3. The method of claim 1 wherein said herbicidally effective amount is from about 10–1000 g. of compound per 10 ares.

4. The method of claim 3 wherein said herbicidally effective amount is from about 50–400 g. of compound per 10 ares.

5. The method of claim 1 wherein said weeds are perennial paddy weeds.

6. The method of claim 1 wherein said compound is employed in dry form.

7. The method of claim 1 wherein said compound is employed in the form of an aqueous suspension.

* * * * *